(12) United States Patent
Krafton et al.

(10) Patent No.: US 6,274,009 B1
(45) Date of Patent: Aug. 14, 2001

(54) GENERATOR FOR GENERATING CHLORINE DIOXIDE UNDER VACUUM EDUCTION IN A SINGLE PASS

(75) Inventors: Brian D. Krafton, Wakefield, RI (US); John C. Smedley, Platte Woods, MO (US)

(73) Assignee: International Dioxide Inc., North Kingston, RI (US)

( * ) Notice: Subject to any disclaimer, the term of this patent is extended or adjusted under 35 U.S.C. 154(b) by 0 days.

(21) Appl. No.: 09/389,335

(22) Filed: Sep. 3, 1999

(51) Int. Cl.[7] .............................. C25B 15/00; C25B 11/00; C25B 11/04
(52) U.S. Cl. ...................... 204/230.2; 204/257; 204/284; 204/290 R; 204/290 F; 204/293
(58) Field of Search ................................. 204/257, 230.2, 204/284, 290 R, 290 F, 293

(56) References Cited

U.S. PATENT DOCUMENTS

| | | | |
|---|---|---|---|
| 2,163,793 | 6/1939 | Logan | 204/9 |
| 2,717,237 | 9/1955 | Rempel | 204/101 |
| 4,432,856 | 2/1984 | Murakami et al. | 204/237 |
| 4,456,510 | 6/1984 | Murakami et al. | 204/101 |
| 4,542,008 | 9/1985 | Capuano et al. | 423/477 |
| 4,683,039 | 7/1987 | Twardowski et al. | 204/95 |
| 4,724,059 | * 2/1988 | Collier | 204/228.2 |
| 5,009,875 | 4/1991 | Kelley | 423/477 |
| 5,084,149 | 1/1992 | Kaczur et al. | 204/101 |
| 5,092,970 | 3/1992 | Kaczur et al. | 204/98 |
| 5,106,465 | 4/1992 | Kaczur et al. | 204/98 |
| 5,158,658 | 10/1992 | Cawlfield et al. | 204/252 |
| 5,294,319 | 3/1994 | Kaczur et al. | 204/290 |
| 5,516,501 | 5/1996 | Kelley | 423/473 |
| 5,868,911 | * 2/1999 | Blum et al. | 204/230.5 X |
| 5,985,109 | * 11/1999 | Hara | 204/257 |
| 5,993,639 | * 11/1999 | Miyashita et al. | 204/257 X |

FOREIGN PATENT DOCUMENTS

| | | |
|---|---|---|
| 714828 | 12/1952 | (GB) . |
| 56-158883 | 12/1981 | (JP) . |

OTHER PUBLICATIONS

"Electrolytic Generation of Chlorine Dioxide", Ebbe R. Skov, P.E. 25th Southern California AICHE Technical Meeting, Anaheim, CA Apr., 1996.

* cited by examiner

Primary Examiner—Donald R. Valentine
(74) Attorney, Agent, or Firm—Margaret B. Kelley; Clifford Chance Rogers & Wells, LLP

(57) ABSTRACT

A vacuum operated electrolytic generator producing a solution of chlorine dioxide from a buffered aqueous alkali metal chlorite solution in one pass through the cell is disclosed. The cell contains a high surface area anode, a corrosion-resistant highly conductive cathode, and a cation ion exchange membrane between the anode and cathode. An eductor is used on the anolyte effluent line to create a vacuum and draw the anolyte through the cell. Preferably, an eductor is used n the catholyte effluent line. Ascending anolyte effluent line with a non-corrosive check valve leads from the cell to the anode eductor. Sensors are used to monitor the composition of the anolyte effluent and/or the anolyte feed.

19 Claims, 9 Drawing Sheets

GENERATOR FOR GENERATING CHLORINE DIOXIDE UNDER VACUUM EDUCTION IN A SINGLE PASS

BACKGROUND OF THE INVENTION

This invention relates generally to the production of chlorine dioxide. More particularly, it relates to an electrolytic generator used to manufacture chlorine-free chlorine dioxide from alkali metal chlorite solutions.

Chlorine dioxide is commercially employed as a bleaching, fumigating, sanitizing or sterilizing agent. Chlorine dioxide can be used to replace the chlorine and hypochlorite products more traditionally used in such applications with resultant benefits. Chlorine dioxide is a more powerful sterilizing agent and requires lower dose levels than chlorine at both low pHs and high pHs, although it is not particularly stable at high pH levels. More importantly, chlorine dioxide produces lower levels of chlorinated organic compounds than chlorine when it is used to sterilize raw water containing organic compounds. Additionally, chlorine dioxide is less corrosive than chlorine to metals.

The electrolytic production of chlorine dioxide is old and well known. See U.S. Pat. No. 2,163,793 issued Jun. 27, 1939 (J. O. Logan); British Patent No. 714,828 published Sep. 1, 1954 (Farbenfabriken Bayer); U.S. Pat. No. 2,717,237 issued Sep. 6, 1955 (Rempel); Japanese Patent application No. 81-158883, published Dec. 7, 1981; and U.S. Pat. No. 4,542,008 issued Sep. 17, 1985 (Capuano et al.).

U.S. Pat. No. 5,084,149 (issued Jan. 28, 1992 to J. J. Kaczur et al. discloses an electrochemical process for manufacturing chlorine-free chlorine dioxide from a diluted alkali metal chlorite solution containing a conductive salt additive in a single step. The electrolytic cell used contains a porous flow-through anode and a cathode separated by a suitable separator.

U.S. Pat. No. 5,092,970 and 5,106,465 (issued Apr. 21, 1992 to J. J. Kaczur et al.) discloses a process for electrolytically producing an aqueous solution of chlorine dioxide in a electrolytic cell having an anode compartment, a cathode compartment, and at least one cation ion exchange compartment between the anode and cathode compartments. An aqueous solution of an alkali metal chlorite is fed to the ion exchange compartment. The anolyte in the anode compartment is electrolyzed to generate hydrogen ions. The hydrogen ions are passed from the anode compartment through the membrane into the ion exchange compartment to displace alkali metal ions and produce an aqueous solution of chlorine dioxide. The alkali metal ions from the ion exchange compartment are passed into the cathode compartment.

In the '465 patent, the use of additives or activators in the chlorite feed solution is disclosed. The additives or activators promote more efficient conversion of chlorite to chlorine dioxide and suppress chlorate formation. Suitable additives include inorganic alkali metal salts and/or chlorides, phosphates, and sulfates and alkali metal tartrates and citrates.

U.S. Pat. No. 5,294,319 (issued Mar. 15, 1994 to J. J. Kaczur et al.) discloses a porous high surface area electrode particularly suitable for use in electrochemical processes.

A disadvantage of the above electrolytic processes is the production of the chlorine dioxide in the anode compartment of the generator so that the chlorine dioxide must be recovered from the anolyte by stripping with air or by some other appropriate means.

The generation and use of chlorine dioxide solutions poses a significant problem because the generation of chlorine-free chlorine dioxide is complex and requires a number of purification steps, including the stripping step discussed above and reabsorbtion of chlorine dioxide from a generating solution to a receiving solution. A stream of air is frequently used for this purpose; however, operation of such a process is hazardous if the chlorine dioxide concentrations in the air become high enough to initiate spontaneous decomposition. U.S. Pat. No. 4,683,039 (Twardowski et al.) discloses a purification method involving the use of a gas-permeable hydrophobic membrane. This purification method reduces the risk of chlorine dioxide decomposition but requires additional costly equipment.

The above problems were solved by employing a continuous electrochemical process and an electrolytic cell containing a porous flow-through anode. Chlorine-free chlorine dioxide was produced in a concentration of at least about 2 to about 10 grams per liter from dilute alkali metal chlorite solutions in a single step. This process and the cell are described in U.S. Pat. No. 5,158,658 issued Oct. 27, 1992 (Cawlfield et al.), the disclosure of which is incorporated herein by reference.

SUMMARY OF THE INVENTION

The present invention provides an electrolytic generator, operated under a vacuum, for producing a solution of chlorine dioxide in one pass by the electrolysis of an anolyte which is a buffered aqueous alkali metal chlorite solution. The generator comprises in combination:

(a) a high surface area, porous anode with multiple electrode posts; (b) a corrosion-resistant, highly conductive cathode with multiple electrode posts; (c) a cation ion exchange membrane which separates the anode and the cathode and forms an anolyte compartment and a catholyte compartment; (d) an array of non-corrosive support ribbings for the cation exchange membrane; (e) a non-binding mesh spacer between the cation exchange membrane and the cathode; (f) catholyte and anolyte cell frames with inlet ports to the catholyte and anolyte compartments at the bottom of the cell frames, with outlet ports from the catholyte and anolyte compartments at the top of the cell frames, and with internal flow distribution headers enclosing the anolyte and catholyte compartments; (g) an anolyte infeed means for introducing the buffered aqueous alkali metal chlorite anolyte into the anolyte compartment, which infeed includes a line with a solenoid followed by a rotameter and a flow switch; (h) an inlet means for softened, deionized, or demineralized purge water, which means includes a line with a solenoid followed by a rotameter and a flow switch, which means is connected to the anolyte infeed line by a juncture and a line leading from the juncture to the anolyte inlet port; (i) a catholyte infeed means for introducing softened, deionized, or demineralized water to the catholyte port, which means includes a line with a solenoid followed by a rotameter and a flow switch; (j) an ascending anolyte outfeed means, connected to the cell frame at the top on the anolyte side, to remove the aqueous chlorine dioxide anolyte effluent from the anolyte outlet port; (k) an eductor connected to the anolyte outfeed means for creating a vacuum in the anolyte compartment by which the anolyte is drawn through the anolyte compartment; (l) a motive water infeed means for supplying water to the eductor; (m) a catholyte outfeed means, connected to the catholyte outlet port, to remove the alkaline hydroxide catholyte effluent containing entrained hydrogen, which means has a non-corrosive check valve (e.g., a plastic check valve) before the eductor; (n) a sensor, connected to the anolyte outfeed means prior to the eductor, for monitoring the anolyte effluent; (o) a pressure switch on the motive water infeed means; and (p) a DC power supply and an automatic current interrupter to prevent reverse current flow across the cell upon shutdown.

Suitable anodes include a fine fibrous conductive substrate, such as titanium, niobium, zirconium, tantalum, aluminum, tungsten, or hafnium, which is optionally coated with a electrocatalyst selected from precious metals (e.g., platinum, silver, or gold), the oxides of platinum group metals, (e.g., the oxides of rutherium, rhodium, palladium, irridium, or osmium), mixtures thereof, or alloys thereof. The anode can be a segmented or unsegmented fibrous titanium anode coated with platinum. The cathode can be a perforated stainless steel plate.

A dilution water infeed means for introducing softened, deionized, or demineralized water into the anolyte infeed line and a juncture joining the dilution water infeed means and the anolyte infeed means are optional. The anolyte in the generator, prior to dilution is about 5% by weight of sodium chlorite buffered at about pH 9.0 and it is about 2% by weight of sodium chlorite.

Also optional are eductors connected to the catholyte outfeed line for creating a vacuum in the catholyte compartment, connected to the dilution water infeed means for creating a vacuum to draw the water into dilution water infeed means; a sensor connected to the anolyte infeed means for monitoring the anolyte infeed; and an on/off valve for the motive water. The catholyte and anolyte infeed and outfeed lines can be plastic tubings (e.g., polypropylene tubings).

A further optional component for use with the generator is an electrical panel containing a sensor, safety indicators, and operation controls. The sensor can be a pH meter, a conductivity probe, an oxidation-reduction potential probe, an amperometric detector, and a colormetric absorption indicator.

The present electrolytic generator is distinguished from prior electrolytic cells by the use of a single anolyte eductor or more preferably separate eductors to generate the vacuum required to draw the anolyte and catholyte feeds through the electrolytic cell. The use of the eductors to create a vacuum in the electrolytic cell allows one to use more concentrated alkali metal chlorite solutions as the anolyte feed. For example, in the vacuum electrolytic generator the anolyte feed can be about 2% or greater by weight of sodium chlorite. In non-vacuum electrolytic cells the anolyte feed can only be 1% by weight of the sodium chlorite. One or more sensors monitor the constituents in the anolyte effluent and/or anolyte feed. The present electrolytic generator also incorporates a number of safety features such as a purge of the generator after the system shuts down or is turned off with softened deionized, or demineralized water, an anolyte effluent line which progressively ascends, without looping back, to the inlet of the anolyte eductor, and sensors to monitor the reaction. The water purge quickly and effectively evacuates the concentrated chlorine dioxide from the anode compartment of the electrolytic generator after the generator shut down. The ascending anolyte effluent line minimizes the possibility that gaseous pockets of chlorine dioxide will form. Such gaseous pockets of chlorine dioxide are potentially explosive. The pH, the electrical conductivity, the oxidation-reduction potential (ORP), the current (amps), or color of the anolyte effluent can be measured using a suitable sensor. The electrical conductivity, current, or OPR of the anolyte infeed can also be measured. If desired, both the infeed and effluent can be monitored.

Another advantage of the vacuum operated electrolytic generator is that it is not necessary to separately remove hydrogen gas produced in the reaction from the catholyte effluent. The entrained hydrogen gas does not impede the cathode effluent flow and does not need to be separated as was customary in prior art electrolytic processes.

The control panel shown on the upper right hand side of the figure contains the operating controls and programmable controller for monitoring safety switches, and sensor(s) used for monitoring the constituents in the anolyte effluent and/or in the anolyte feed.

Figure 2:
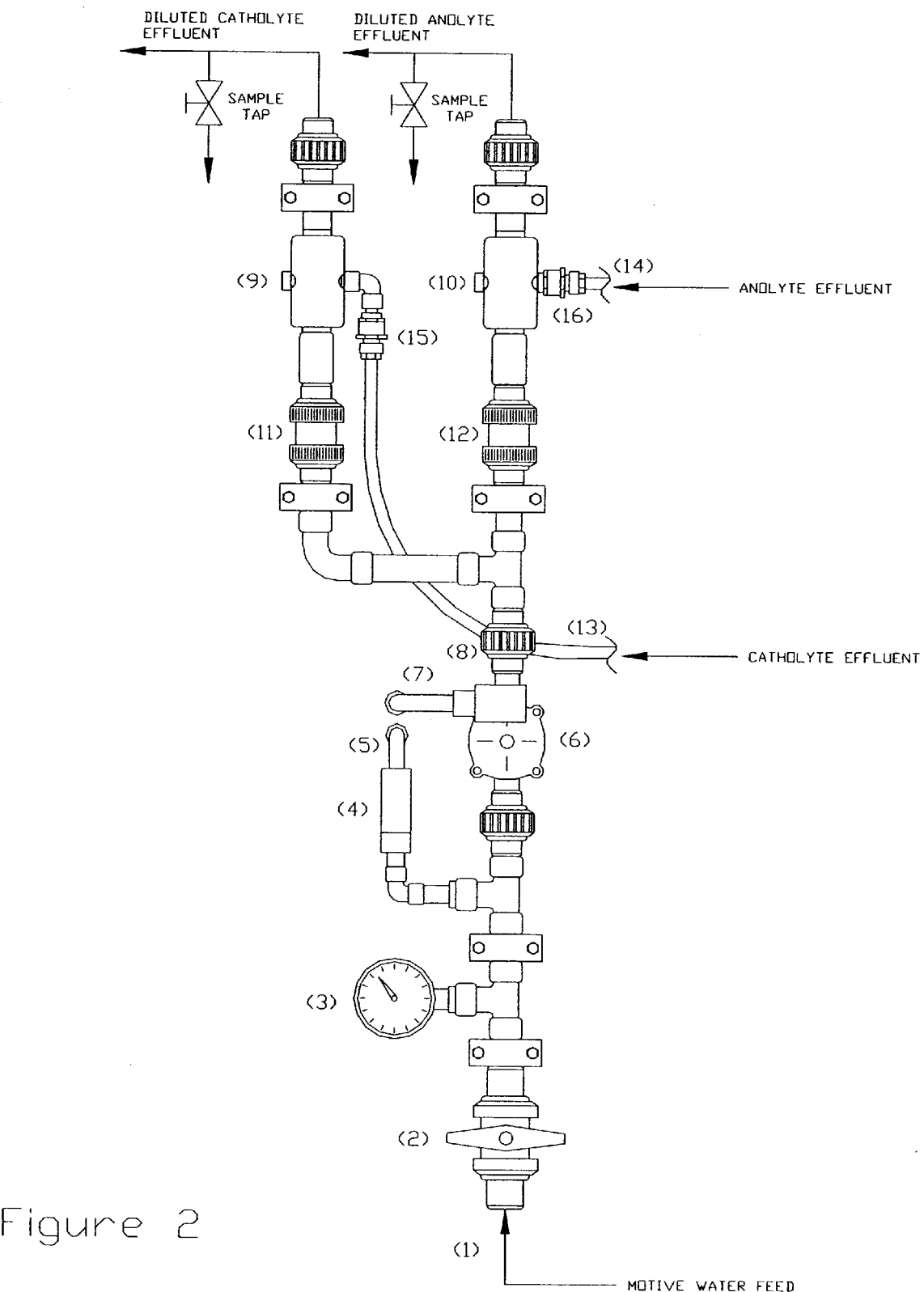

FIG. 2 shows the input line (1) is for the motive water feed. On/off valve (2) controls for the motive water feed. Pressure gauge (3) and pressure switch (4) monitoring the motive water pressure and provide an alarm signal for undesirable pressure conditions. Conduit line (5) runs from pressure switch (4) to the electrical panel shown in FIG. 6. Solenoid (6) is connected to motive water line (1). Conduit line (7) runs from solenoid (6) to the electrical panel shown in FIG. 6. Union (8) joins the catholyte eductor (9) and anolyte eductor (10). Eductor (9) and (10) create sufficient vacuum to draw the catholyte and anolyte flows through the electrochemical cell. Inline ball check valves (11) and (12), respectively, prevent back flow through eductors (9) and (10). Catholyte and anolyte effluents are educted from the electrolytic cell through plastic tubings (13) and (14), respectively. The anolyte effluent tubing (14) progressively ascends, with no back looping or horizontal sections, to the inlet of anolyte eductor (10) so as to minimize the possible formation of gaseous pockets of chlorine dioxide. Such pockets are potentially explosive. Non-corrosive check valves (15) and (16), respectively, are present on the catholyte and anolyte tubings (13) and (14), respectively, to prevent back flow through the electrolytic cell and prevent inadvertent over hydraulic pressurization of the cell. Optional sample taps are typically located on the catholyte and anolyte discharge lines as illustrated.

Figure 3:
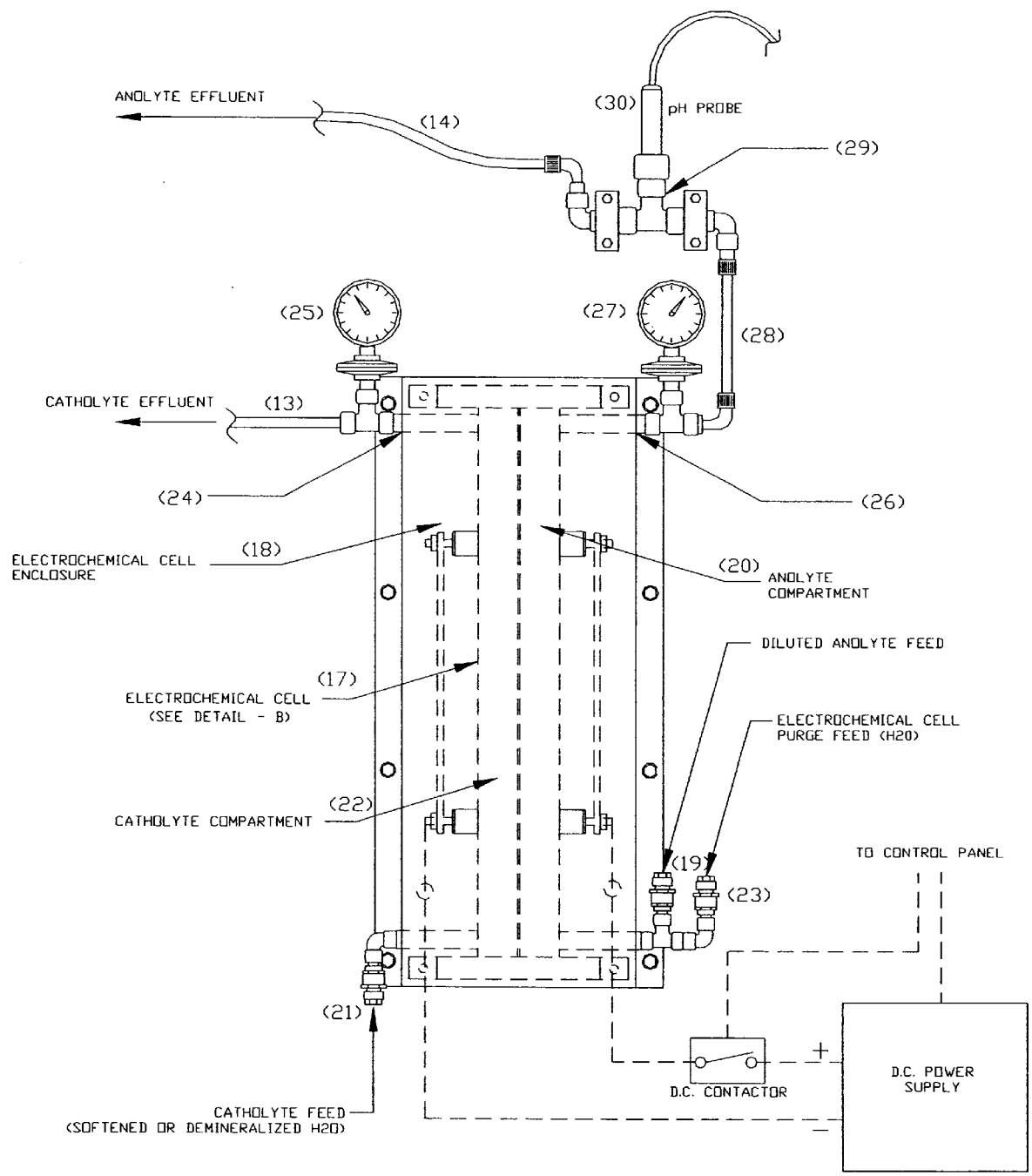

FIG. 3 shows electrolytic cell (17) and cell enclosure (18). The sensor shown is pH probe (30) which is used to monitor anolyte effluent. Although not shown, other sensors can be used to monitor anolyte effluent. In addition, (also not shown) an ORP detected conductivity sensor could be used to monitor the anolyte feed. Inlet (19) for the anolyte feed, which is the diluted buffered aqueous alkali metal chlorite solution, leads into the anolyte compartment (20). Inlet (21) for the catholyte feed, which is the softened or demineralized water, leads into the catholyte compartment (22). Water purge feed line (23) is connected to the diluted anolyte feed line (19). Exit (24) for the catholyte effluent is connected by tubing (13) to the catholyte eductor (9) through check valve (15). Catholyte effluent vacuum gauge (25) is located after exit (24). Exit (26) for the anolyte effluent is connected by tubing (28) to probe holder (29) where a probe (30) is inserted to measure the pH, electrical conductivity, or oxidation-reduction potential of the anolyte effluent before it enters tubing (14) for reduction into the anolyte eductor (10) through check valve (16). Anolyte effluent vacuum gauge (27) is located between exit (26) and the sensor holder (29) and sensor (30). Sensor (30) is connected to the control panel shown in FIG. 7.

Figure 4:
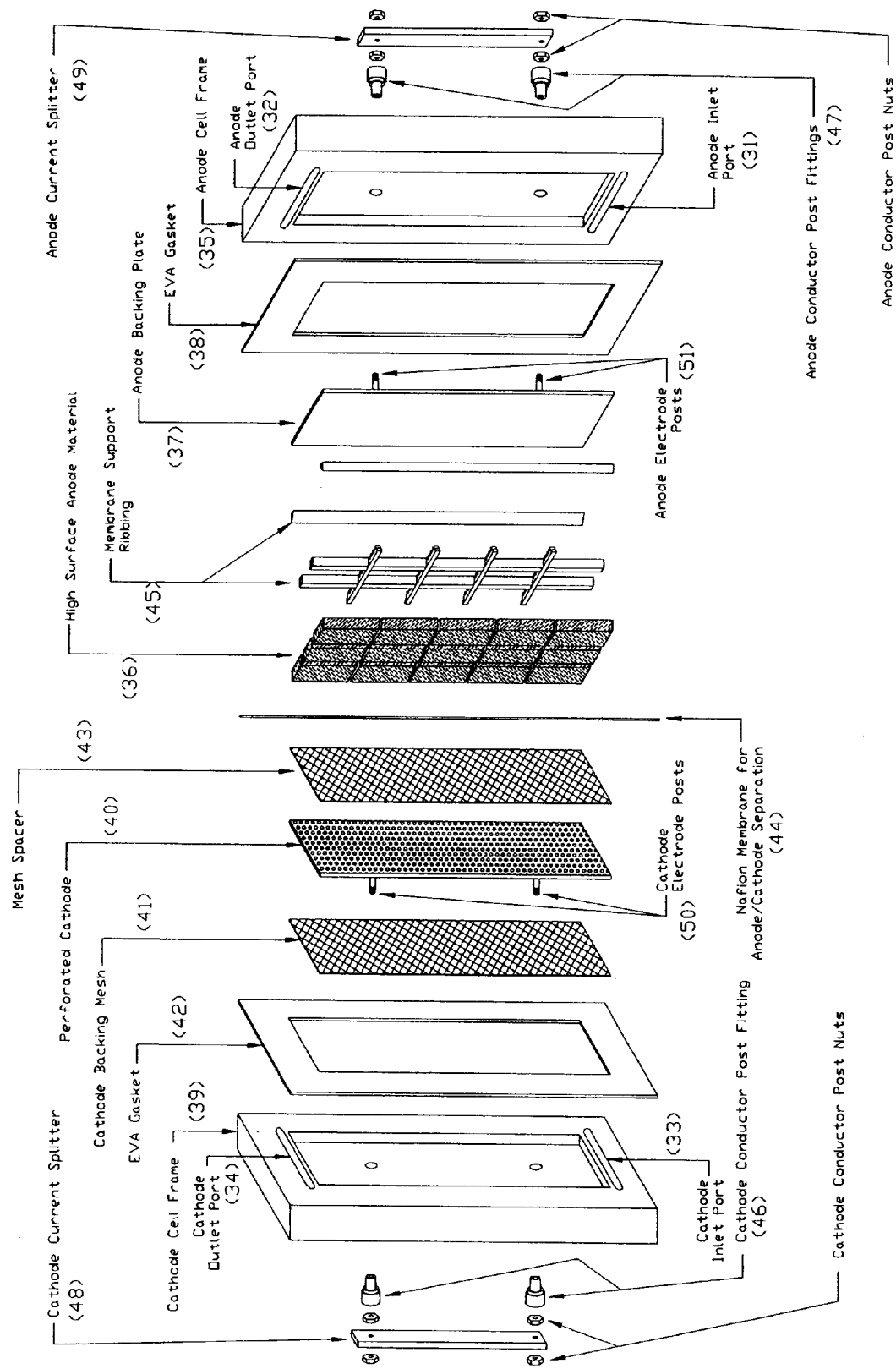

FIG. 4 shows the configuration of the interior of the electrolytic cell (17). The anolyte inlet port (31) and anolyte outlet port (32) are shown on the right. The catholyte inlet port (33) and exit port (34) are shown on the left. Between the anode cell frame (35) and the high surface area anode (36) is an anode backing plate (37) and a perimeter-sealing plastic gasket (38). Catholyte inlet and outlet ports (33 and 34) are shown on the left side of cell frame (39). Between the cell frame (39) and the perforated cathode (40) is a cathode backing mesh (41) and a plastic gasket (42). Between the high surface area anode (36) and the mesh spacer (43) is cation exchange membrane (44). Also shown are the membrane support ribbings (45), cathode conductor post fittings (46), anode conductor post fittings (47), cathode and anode current splitters (48) and (49), and cathode and anode conductor post nuts. The cathode conductor post fittings (46) provide a liquid tight seal around the cathode conductor posts (50). The anode conductor post fittings (47) provide a liquid tight seal around the anode conductor posts (51).

Figure 5:
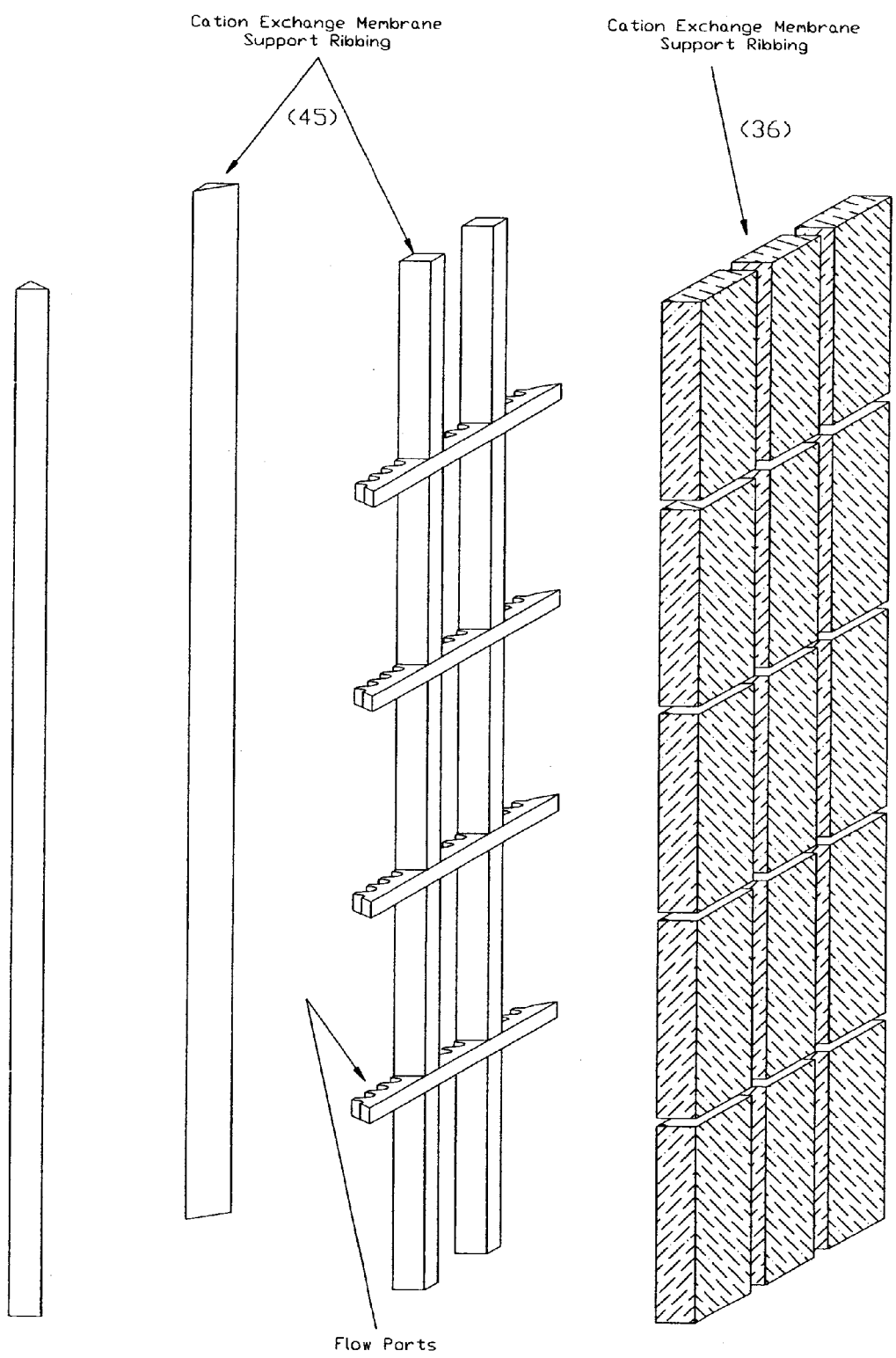

FIG. 5 shows the high surface area anode (36) segmented into sections to fit into each of the corresponding areas of the membrane support ribbing (45). The membrane ribbing support (45) is designed to provide adequate support of the cation exchange membrane (44) while allowing free flow of anolyte through the anode cell frame (35) from the anode inlet port (31) to the anode outlet port (32).

Figure 6:
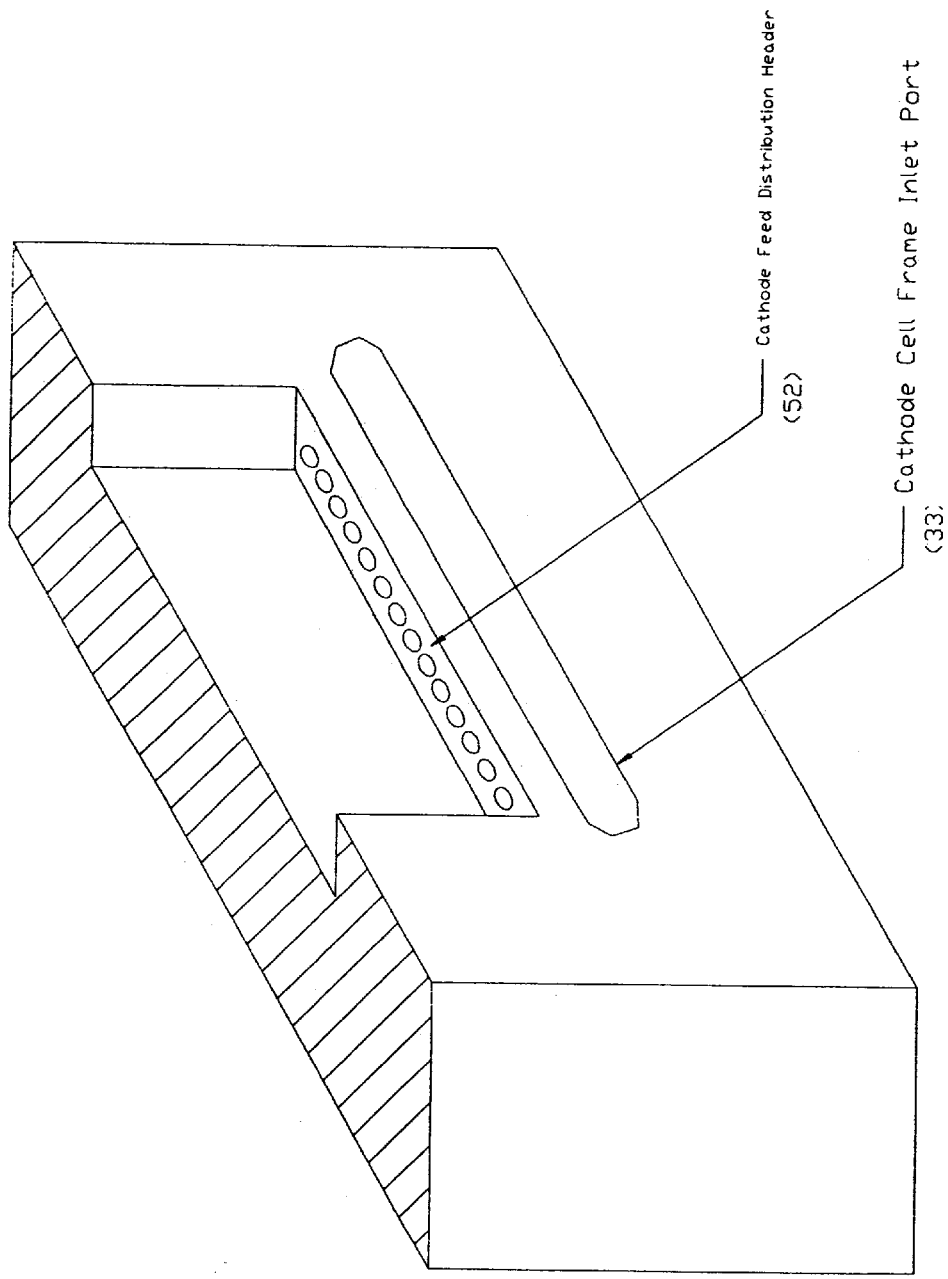

FIG. 6 shows the distribution header arrangement (52) with multiple flow ports for the cathode inlet port (33). Similar distribution header arrangements are present for the anode inlet port (31), cathode inlet port (34), and anode outlet port (32). The design of the distribution header is such that there is a sufficient pressure drop across the header to ensure evenly distributed flow through each distribution header and each individual flow port.

Figure 7:
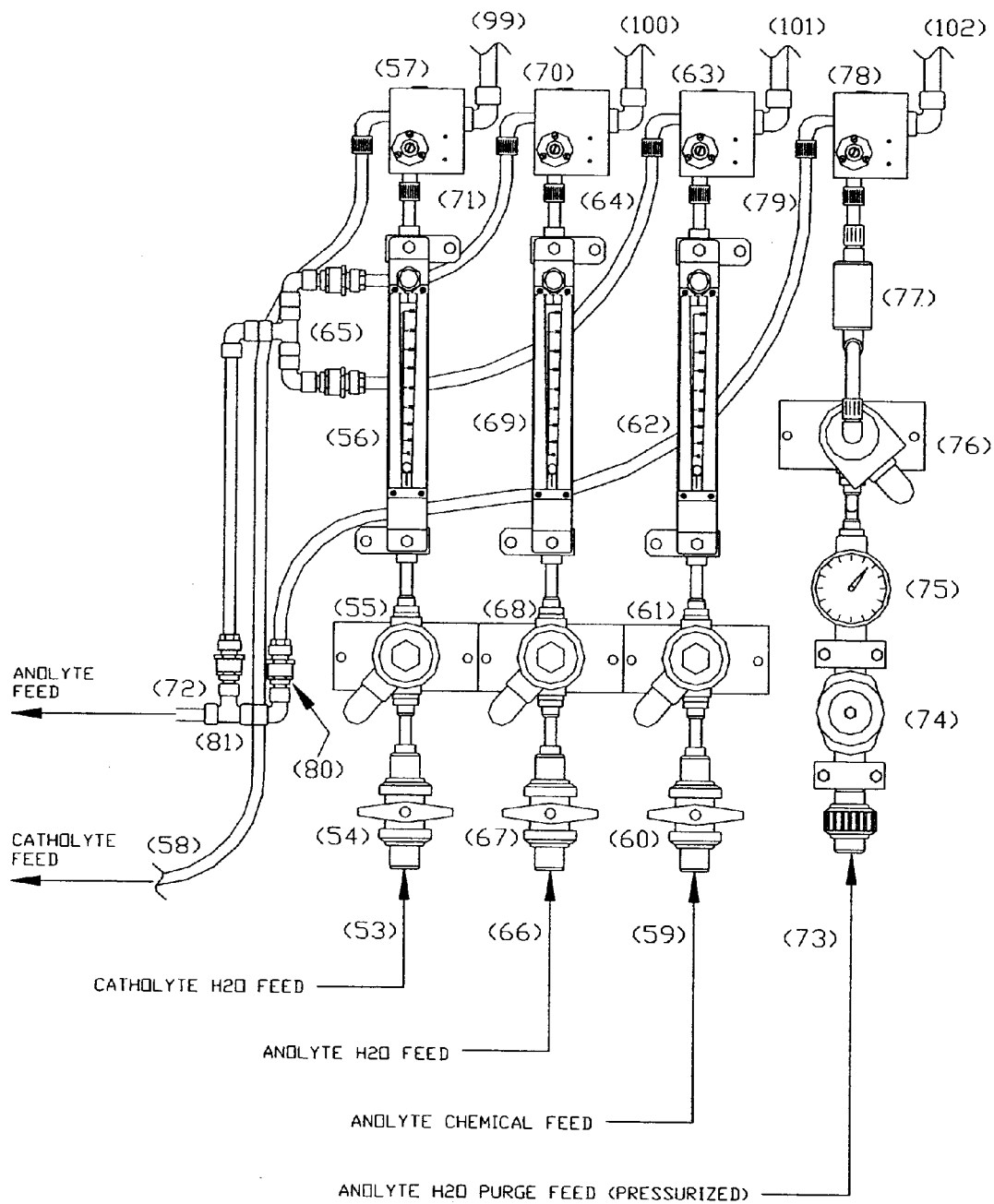

FIG. 7 shows the feed lines to the electrolytic cell (17). Catholyte water feed line (53) is controlled by on/off valve (54). The catholyte water then passes through solenoid (55) to flow controlling rotameter (56) through flow switch (57) and into tubing (58) which leads into catholyte inlet check valve (21) of the electrolytic cell frame (22). Anolyte feed line (59) passes undiluted anolyte chlorite feed through on/off valve (60). The undiluted anolyte feed passes through solenoid (61) to flow controlling rotameter (62) and through flow switch (63) and into tubing (64) which leads to junction (65) Anolyte water feed line (66), which provides the softened, deionized, or demineralized water for diluting the buffered alkali metal chlorite introduced into the anolyte feedline (59) passes through on/off valve (67). The softened, deionized or demineralized water passes through solenoid (68) to rotameter (69), through flow switch (70), and into tubing (71) which connects with junction (65). From junction (65) the diluted anolyte passes through tubing (72) into the anolyte inlet of the anode electrolytic cell frame (20). Non-corrosive (e.g., Teflon) check valve (13) eliminates possible back flow of anolyte through inlet of the anode electrolytic cell frame (20). A water purge for the anolyte chamber (20) is introduced through inlet (73), pressure regulator (74), pressure gauge (75) into solenoid (76), flow control valve (77), and flow switch (78). A non-corrosive (e.g., plastic) feed line (79), leads through a non-corrosive check valve (e.g., Teflon) (80) into junction (81) joining the diluted anolyte feed line before it enters inlet tubing (15) of the electrolytic cell frame (20).

Figure 8:
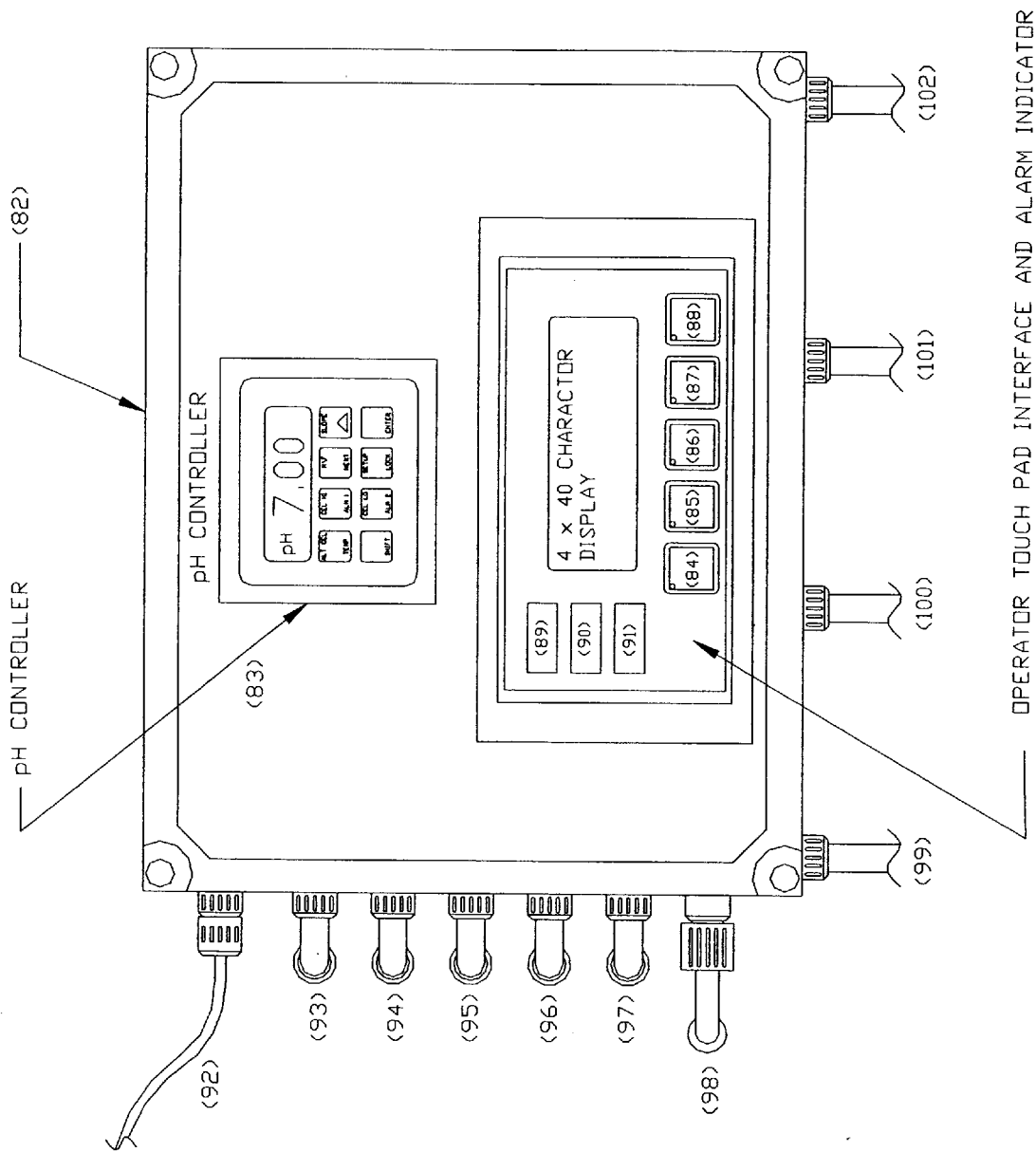

FIG. 8 shows the control panel (82) which contains probe controller (83), shown here as a pH meter, in the center. Operator touch pads (84), (85), (86), (87), and (88) are for start/stop, automatic operation booster pump on, alarm silencer, and alarm reset, respectively. Indicators (89), (90), and (91) are for alarm, purge, and run, respectively. Sensor connection (92) leads into control panel (82). Solenoid conduits (93), (94), (95), (96), and (97) are for the motive eductor water, catholyte water, undiluted anolyte feed, anolyte dilution water, and purge water, respectively. Pressure switch conduit (98) relays the electrical signal to the control panel (82) to monitor the motive water pressure. Flow switch conduits (99), (100), (101), and (102) are for the catholyte water, anolyte dilution water, anolyte feed, and purge water, respectively.

Other features and advantages of the present invention will become apparent upon consideration of the following detailed disclosure of the invention, especially when it is taken in conjunction with the above figures.

BRIEF DESCRIPTION OF THE SEVERAL VIEW OF THE DRAWINGS

Figure 1:
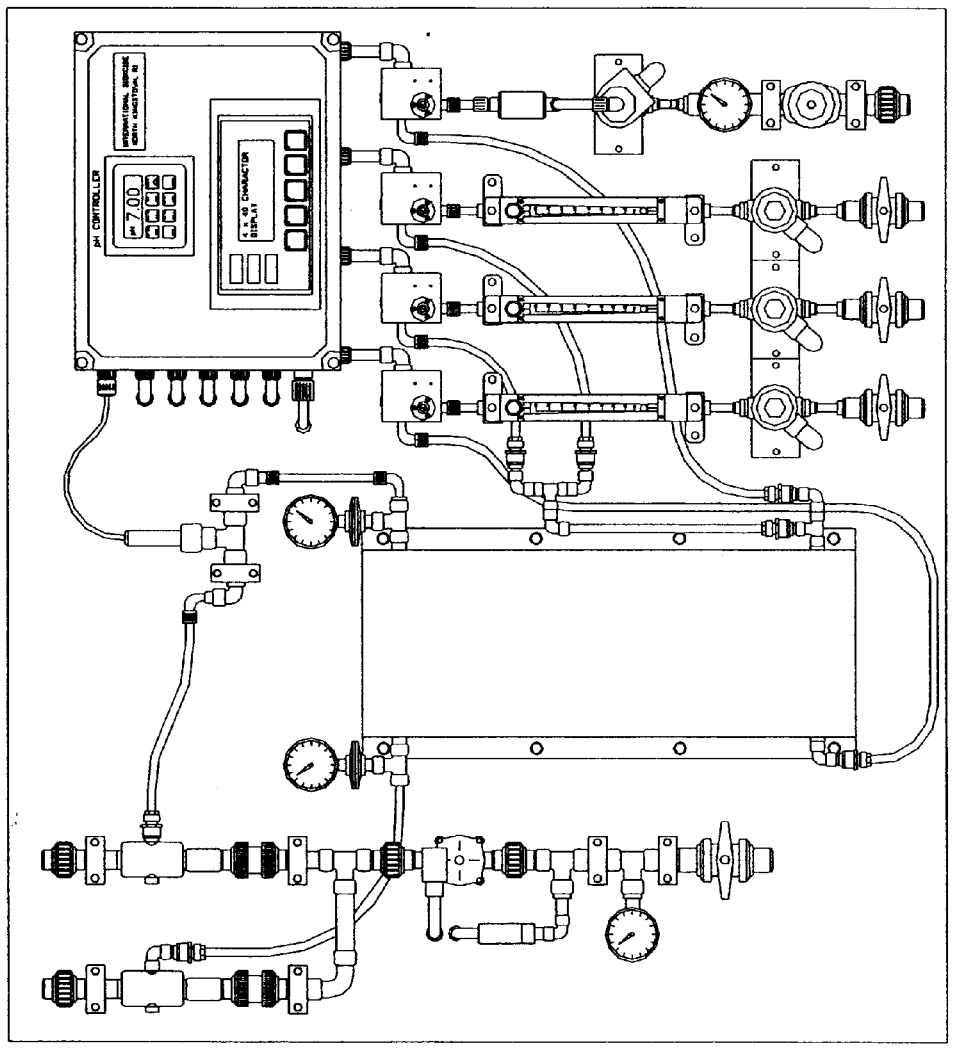
FIG. 1 schematically depicts an electrolytic generator, such as the process of Cawlfield et al., for producing chlorine dioxide in a single pass using an anolyte feed which can be diluted during operation of the generator. The generator is operated under a vacuum created by a single anolyte eductor or more preferably by separate anolyte and catholyte eductors jointly connected to a motive water line. The preferred eductors and motive water inlet are shown on the left side of FIG. 1. The electrolytic cell is shown in the center of FIG. 1. The cell contains a high surface area anode and a perforated cathode separated by a cation permeable ion exchange membrane. The membrane divides the cell into catholyte and anolyte compartments having inlets at the bottom for the anolyte and catholyte feed and outlets at the top for the anolyte and catholyte effluents. The membrane is supported on the anode side of the cell by an array of non-corrosive support ribs. These ribs minimize deflection of the membrane towards the anode chamber of the cell where compression of segmented or unsegmented high surface area anode could occur. A non-binding mesh spacer separates the membrane from the cathode. The feed lines and flow switches for the anolyte feed, catholyte feed, dilution water and water purge are shown on the lower right of FIG. 1. The anolyte feed consists of an undiluted, buffered aqueous alkali metal chlorite solution, e.g., an aqueous solution of 5 wt. % sodium chlorite buffered to about pH 9.0 with buffers, e.g., sodium carbonate/sodium bicarbonate, sodium diphosphates/sodium hydrogen phosphate, citrates, and the like. The catholyte feed consists of softened deionized, or demineralized water. Softened, deionized or demineralized water is also used for the anolyte feed dilution and purge feed.
Figure 1A:
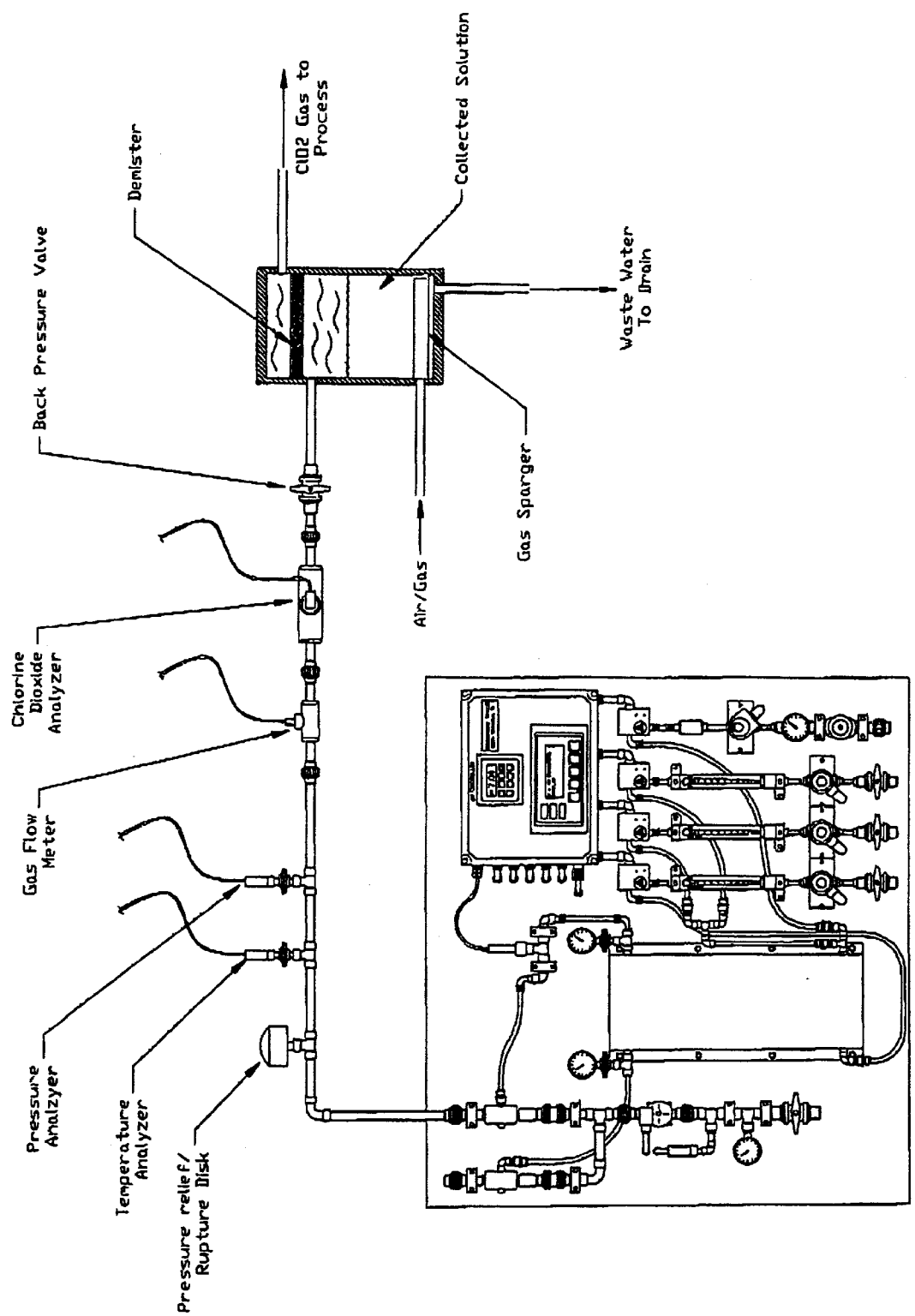

FIG. 1 shows an electrolytic generator for producing a solution of chlorine dioxide in one pass by the electolysis of an anolyte which is a buffered aqueous alkali metal chloride solution.

FIG. 2 shows a front view of the motive water infeed means.

FIG. 3 shows a side view of the electrochemical cell and electrochemical cell outfeed means.

FIG. 4 shows an exploded side elevation view of the electrochemical cell.

FIG. 5 shows an exploded side elevation view of the high surface area, porous anode and membrane support ribbing.

FIG. 6 shows the typical distribution header arrangement for the cathode inlet ports, cathode outlet port, anode inlet port, and anode outlet port.

FIG. 7 shows the front view of the electrochemical cell infeed means.

FIG. 8 shows the front view of the control panel and operator interface.

DESCRIPTION OF THE PREFERRED EMBODIMENTS

The membrane used to divide the electrolytic cell into anolyte and catholyte compartments is an oxidation-resistant, cation-permeable ion exchange membrane. Appropriate sealing means, such as gaskets or an O-ring, are used to create a liquid-tight seal between the membrane and the cell frame.

A suitable cathode is an electrode made of smooth, perforated stainless steel. The cathode is positioned in the cathode cell frame between the cathode backing mesh and the mesh spacer which separate the cathode and the cation-permeable ion exchange membrane. The preferred structure of the cathode is a smooth, perforated stainless steel of grades such as 304, 316, 310, and the like. The perforations should be large enough to permit release of hydrogen bubbles from between the membrane and the cathode. Other suitable cathode materials include nickel or nickel-chrome based alloys. Titanium or other valve metal cathode structures can also be used. A corrosion resistant alloy is preferred to reduce formation of some localized iron corrosion by products on the cathode surface due to potential chlorine dioxide diffusion through the membrane by surface contact with the cathode. Other suitable materials for the cathode include fine woven wire structures on an open type metal substrate, which can help to reduce the cell voltage by promoting hydrogen gas bubble disengagement from the surface of the cathode.

Multiple cathode conductor posts transmit electrical current from a power supply (not shown) through current splitter wire and cathode conductor post nuts to the cathode. Cathode conductor post fittings extend into the cathode frame about posts to seal against posts and prevent the leakage of catholyte from the cell.

The anode side of the cell contains a porous, high surface area anode and an anode backplate or current distributor fitted within the compartment. The anode is an electrode made of a porous and high surface area material. The high surface area material increases the rate of mass transport into and away from the surface of the anode and distributes the current so that the rate of charge transfer from the electrode to the anolyte solution is much lower than the rate of charge transfer through the membrane and the electrolyte. Materials with a surface area to volume ratio of about 50 $cm^2/cm^3$ or higher are suitable for achieving a high percentage conversion of chlorite to chlorine dioxide. Higher surface area to volume ratios are more desirable up to the point where the pressure drop becomes critical. The anode must be sufficiently porous to permit the anolyte to pass through it during operation. The porosity must also be sufficient so that the effective ionic conductivity of the solution inside the electrode is not substantially reduced. Anodes with a void fraction of greater than about 40% are suitable to accomplish this.

Preferred high surface area porous anodes are disclosed in U.S. Pat. No. 5,294,319 (issued Mar. 15, 1994 to Kaczur et al.), the disclosure of which is incorporated by reference.

A thin deposited platinum conductive coating or layer on a corrosion resistant high surface area ceramic, or a high surface, a titanium fiber structure, or a plastic fiber substrate can also be used.

Multiple anode conductor posts transmit electrical current from a power supply (not shown) through current splitter wire and anode conductor post nuts to the anode 14. Anode conductor post fittings extend into the anode frame about posts to seal against posts and prevent the leakage of anolyte from the cell.

The anolyte current distributor or backplate distributes the current evenly to the flexible and compressible porous, high surface area anode which does most of the high efficiency electrochemical conversion of the chlorite solution to chlorine dioxide.

A porous high surface area material of a compressible graphite felt or cloth construction can be used as the anode. The graphite surfaces can be impregnated with metallic films or metallic oxides to increase the life of the graphite. Other alternatives include fluoride surface-treated graphite structures which are used to improve the anodes useful life by preventing degradation due to the generation of small amounts of by-product oxygen on the surface of the graphite. Since such graphite structures are relatively inexpensive, they can be used as disposable anodes that can be easily replaced after a finite period of operation.

The anode backplate or current distributor can be similarly made of a graphite material which can be surface-treated with agents such as those used on the porous, high surface area anode material. Other alternative materials suitable for use in the current distributor include metallic films or metallic oxides on stable, oxidation-resistant valve metal structures such as titanium, tantalum, niobium, or zirconium. The coatings include metallic platinum, gold, or palladium coatings, or other precious metal coatings or oxide coatings.

A suitably diluted alkali metal chlorite feed solution, preferably sodium or potassium chlorite, is fed into anolyte compartment through the anode feed inlet and anolyte solution distributor channels at a suitable flowrate to allow for the electrochemical conversion of the chlorite ion to chlorine dioxide by the flexible, compressible, porous, high oxygen over voltage, high surface area anode. The electrical current is conducted to the high surface area anode by the high oxygen over voltage anode backplate or current distributor which has one or more metallic anode conductor posts to conduct the DC electrical power from a DC power supply (not shown). Fittings are used to seal against conductor posts to prevent solution leakage from the cell. Current splitter wire and anode conductor post nuts are used to distribute the electrical current to the anode distributor. The resulting chlorine dioxide solution (anolyte effluent) exits through the anode outlet.

Softened, deionized, or demineralized water is educted into the catholyte inlet port and catholyte distribution orifices into the catholyte compartment at a flowrate sufficient to maintain a suitable operating concentration of alkali metal hydroxide in the catholyte. The alkali metal hydroxide is formed by alkali ions (not shown) passing from the anolyte compartment through the cation permeable ion exchange membrane into catholyte compartment and by the electrical current applied at the cathode to form the hydroxyl ions (OH$^-$) at the cathode surface. The reaction at the cathode produces hydrogen gas, as well as hydroxyl ions, from the electrolysis of water. The catholyte alkali metal hydroxide solution by-product and hydrogen gas (not shown) pass through the cathode compartment into the catholyte outlet for removal from the cell under vacuum through the catholyte effluent tubing catholyte eductor check valve and into the catholyte eductor.

Electrolysis occurs in the cell as the chlorite solution passes parallel to the membrane through the anolyte compartment, causing the chlorine dioxide concentration to increase in the anolyte compartment as the chlorite ion concentration decreases according to the following reaction at the anode:

$$ClO_2^- \rightarrow e^- + ClO_2.$$

Alkali metal ions, for example, sodium (Na⁺), from the anolyte pass through the membrane. As the chlorite ion content of the anolyte decreases and the chlorine dioxide content increases, a portion of the chlorine dioxide can be oxidized at the anode, depending upon the pH, to the undesirable chlorate according to the following reaction:

$$ClO_2 + H_2O \rightarrow HClO_3 + H^+ + e^-.$$

This undesirable reaction can be avoided by maintaining a suitably acidic anolyte, and especially at higher pH's, by controlling the potential at the anode surface while providing mass transport of the chlorite ions from the bulk solution to the anode surface and transport of chlorine dioxide away from the anode surface. This permits high chlorine dioxide yields to be obtained.

The gaskets are preferably made of an oxidation-resistant rubber or a plastic elastomeric material. Suitable of gaskets are those made from rubber-like materials such as EVA or EPDM or gaskets sold under the trademark Viton®, and the like. Other suitable gasket materials include flexible closed foam types made from polyethylene, or polypropylene, or EVA (Ethyl Vinyl Acetate) which can be easily compressed to a thin layer to minimize distances between the membrane and the anode and cathode structures.

Oxidation and high temperature resistant membranes are preferred. Among these are perfluorinated sulfonic acid type membranes such as DuPont NAFION® types 117, 417, 423, 450 and the like, membranes such as those disclosed in U.S. Pat. No. 4,470,888, and other polytetrafluorethylene-based membranes with sulfonic acid groups such as those sold under the RAIPORE tradename by RAI Research Corporation. types of membranes that are membranes having combinations of sulfonic acid/carboxylic acid moieties, including those sold under the ACIPLEX tradename by the Asahi Chemical Company and under the FLEMION® trademark by the Asahi Glass Company.

A non-blinding thin mesh spacer can also be used between the cathode and the membrane. The spacer used in the catholyte compartment should also be a non-conductive plastic with large enough holes for ease of disengagement of the hypdrogen gas from the catholyte compartment. The generator preferably is operated with the membrane of the cell in contact with the non-binding plastic spacer and the spacer material when they are employed and with the membrane in contact with the cathode electrode and the anode electrode when they are not employed.

The preferred anolyte feed solution is sodium chlorite with a feed concentration of about 0.1 to about 30 gpL for one-pass through flow operation.

Additives in the form of salts, such as alkali metal phosphates, sulfates, chlorides and the like, can be used in the chlorite feed solution to increase the conversion efficiency, to reduce operating voltage to provide pH buffering of the final product solution, or add to stabilize the chlorine dioxide solution during storage.

In operation, the cell operates with the electrolytes at a temperature of from about 5° C. to about 50° C., with the preferred operating temperature being about 10° C. to about 30° C. The preferred method of introducing the anolyte feed, e.g., buffered sodium chlorite solution, is to dilute it in line on the generator, by mixing with softened or deionized water to the desired concentration before it enters the anolyte compartment. (see FIG. 7) An alternative would be to pre-dilute the anolyte feed solution (undiluted sodium chlorite) separate from the electrochemical generator by using an eductor which is designed to automatically draw in the undiluted sodium chlorite under vacuum and dilute it to the users desired concentration. This predituled solution can then be used as a single anolyte feed to the electrochemical cell without the need to additional dilution and/or preparation. The catholyte is either deionized water or softened water, depending on what is readily available and depending on whether the by-product sodium hydroxide has a potential end use in other areas of the installation, e.g., for controlling pH.

The cell uses an operating current density of from about 0.01 KA/m2 to about 10 KA/m2, with the preferred range being about 0.05 KA/m2 to about 3 KA/m2. The constant operating cell voltage and electrical resistance of the anolyte and catholyte solutions are limitations of the operating cell current density that must be traded off or balanced with current efficiency and conversion yield of chlorite to chlorine dioxide. The cell operating voltage depends on the oxygen over voltage of the anode materials used in the anode structures. The higher the oxygen over voltage of the anode materials, the higher the voltage at which the generator can be operated and still maintain a high current efficiency and yield chlorine dioxide. The typical operating voltage range is between about 2.0 to about 7.0 volts, with a preferred range being about 2.5 to about 4.0 volts.

Additionally, the ratio of the total surface area of the anode to the superficial surface area or projected area of the membrane impacts the current density at which the generator can be operated and the total generator voltage. The higher that this particular ratio is, the greater is the maximum current density, and the lower is the total generator voltage, at which the generator be operated.

The anolyte flow rate through the cell 10 and the residence time of the anolyte in the cell are factors that affect the conversion efficiency of chlorite to chlorine dioxide. There are optimum flow rates to achieve high efficiency conversion and to obtain the specific pH final product solution needed for the commercial applications for a single pass flow through system. The typical pH range is about 2.5 to about 8.0. Typical residence times for the single pass flow through system in the cell to achieve high conversion of chlorite to chlorine dioxide with high current efficiency are between about 0.1 to about 10 minutes, with a more preferred range being about 0.5 to about 4 minutes. Very long residence times can increase chlorate formation as well as reduce the pH of the product solution to very low values (i.e., pH 2 or below) which may be detrimental to the anode structures.

The catholyte and by-product sodium hydroxide concentration should be about 0.1 to about 30% weight, preferably about 0.5 to about 10 weight %. The optimum hydroxide concentration will depend on the membrane's performance characteristics. The higher the caustic or sodium hydroxide concentration, the lower is the calcium concentration or water hardness needed for long life operation of the membrane.

Analytical Test Method For Determining Chlorine Dioxide Concentration and Conversion The sample to be tested is obtained by placing a flexible hose to the sample port's barbed fitting, running this hose to the bottom of the amber sample bottle, and slowly and completely filling the bottle with anolyte effluent from the generator. The bottle should be capped and the analysis should be immediately carried out.

Free Oxidants

The free oxidants are determined by placing ~100 mls of deionized (D.I.) water into an erlenmeyer flask and adding Potassium Iodide Powder Pillow (#1077-99), adding 1 ml of pH 7 Buffer, Phosphate Type (#21553-32), then adding 1–2 ml (V) of generator effluent beneath the surface of the D.I. water using a 0.113N (N) Sodium Thiosulfate Titration Cartridge (#22673-01) and a digital titrator, add the titrant until the solution turns a straw yellow color, then add a few drops of starch solution (#349-32) before titrating the solution to a colorless endpoint.

$$A = \frac{(digits/800)}{V(mls)}$$

Total Oxidants

The total oxidants are determined by adding to the above sample one Dissolved Oxygen Powder Pillow (#987-99), allowing the reaction to take place in the dark for 5 minutes, and titrating to a colorless endpoint using a 0.113N (N) Sodium Thiosulfate Titration Cartridge (#22673-01) and a digital titrator. Add the titrant until the solution turns a straw yellow color, then add a few drops of starch solution (#349-32) before titrating the solution to a colorless endpoint.

$$B = \frac{(digits/800)}{V(mls)}$$

Unsparged Chlorine

The unsparged chlorine is determined by placing ~100 mls of D.I. water into an erlenmeyer flask, adding 1 ml of pH 7 Buffer, Phosphate Type (#21553-32), and then adding 1–2 ml (V) of anolyte effluent from the generator beneath the surface of the water. The solution is sparged for 15 minutes using a gas dispersion tube and an inert gas (either nitrogen or helium), and then adding one Potassium Iodide Powder Pillow (#1077-99). Using a 0.113N (N) Sodium Thiosulfate Titration Cartridge (#22673-01) and digital titrator and the titrant until the solution turns straw yellow color, then add a few drops of starch solution (#349-32) before titrating to a colorless endpoint.

$$C = \frac{(digits/800)}{V(mls)}$$

Unreacted Chlorite

The unreacted chlorite is determined by adding to the above sample one Dissolved Oxygen Powder Pillow (#987-99). The mixture is allowed to react in the dark for 5 minutes. Using a 0.113N (N) Sodium Thiosulfate Titration Cartridge (#22673-01) and digital titrator, add the titrant until the solution turns a straw yellow color, then add a few drops of starch solution (#349-32) before titrating to a colorless endpoint.

$$D = \frac{(digits/800)}{V(mls)}$$

All of the reagents necessary to carry out the above tests are available from Hach, Inc. P.O. Box 389, Loveland, Colo. 80539-9986. The following calculations are used to determine the parts per million (ppm) of chlorite ($ClO_2^-$), chlorine dioxide ($ClO_2$), and chlorine ($Cl_2$), the efficiency, i.e., conversion, and excess chlorine ($Cl_2$).

ppm $ClO_2^- = 5/4 \times (B-D) \times N \times 13,490$ ppm $ClO_2 = D \times N \times 16,863$ ppm $Cl_2 = [A-(B-D)/4] \times N \times 35,450$ $$\text{Efficiency} = \frac{ClO_2 \times 100\%}{ClO_2 + ClO_2^-}$$

$$\text{Excess } Cl_2 = \frac{Cl_2/35.45 \times 100\%}{[(ClO_2 + ClO_2^-)/67.45]}$$

In order to exemplify the results achieved, the following examples are provided without intent to limit the scope of the present invention to the discussion therein.

EXAMPLE 1

An Oxychlor e(Trademark of International Dioxide, Inc.) chlorine dioxide generator was tested by feeding a diluted solution of sodium chlorite (2%) buffered at about pH 9 with a sodium carbonate/bicarbonate to the anolyte compartment. While the anolyte solution was educted through the anode compartment of the electrolytic cell softened water was pumped through the cathode compartment of the electrolytic cell. This is also the case for subsequent examples 2, 3, and 4 below. The cell described in the preceding figures has support ribbings for the membrane.

The results are shown below in Table 1.

TABLE 1

| Power | | Anolyte | | Catholyte | | Conversion | | |
|---|---|---|---|---|---|---|---|---|
| | | | Vacuum | | Pressure | | $ClO_2$ | |
| Volts | Amps | gpd | (psig) | gpd | (psig) | pH | Titrations | (%) |
| 4.31 | 80 | 65 | 10.3 | 85 | 3 | 3.0 | A = 95<br>B = 625 | 72 |
| 4.35 | 83 | 65 | 10.3 | 85 | 3 | 4.5 | A = 89<br>B = 761 | 53 |
| 4.29 | 81 | 65 | 7.4 | 85 | 3 | 3.0 | A = 76<br>B = 498 | 72 |

The added membrane support ribbing on the anode side of the electrolytic cell significantly improved the conversion, as shown by the comparative data shown in Tables 2, 3, 4, and 5 below. The same generator was used but the electrolytic cell contained no support strips for the membrane.

TABLE 2

| Power | | Anolyte | | Catholyte | | Conversion | | |
|---|---|---|---|---|---|---|---|---|
| | | | Vacuum | | Pressure | | $ClO_2$ | |
| Volts | Amps | gpd | (psig) | gpd | (psig) | pH | Titrations | (%) |
| 4.39 | 97.5 | 57[a] | 10.8 | 85 | 3 | 3.1 | A = 38<br>B = 506 | 32.5 |
| 4.44 | 97.5 | 57[a] | 10.8 | 85 | 3 | 3.3 | A = 56<br>B = 638 | 38.5 |
| 4.43 | 97.5 | 58[a] | 10.8 | 85 | 3 | 3.5 | A = 46<br>B = 650 | 30.5 |
| 4.38 | 82 | 65[b] | 10.3 | 85 | 3 | 3 | A = 46<br>B = 552 | 36 |
| 4.37 | 80 | 65[b] | 10.3 | 85 | 3 | 3.28 | A = 43<br>B = 535 | 35 |
| 4.32 | 77.5 | 65[b] | 10.3 | 85 | 3 | 3.5 | A = 42<br>B = 541 | 33.7 |
| 3.87 | 67.5 | 50.5[c] | 10.3 | 65 | 3 | 3 | A = 38<br>B = 438 | 38 |

TABLE 2-continued

| Power | | Anolyte | | Catholyte | | | Conversion | |
|---|---|---|---|---|---|---|---|---|
| | | Vacuum | | Pressure | | | $ClO_2$ | |
| Volts | Amps | gpd | (psig) | gpd | (psig) | pH | Titrations | (%) |
| 3.89 | 66 | 50.5[c] | 10.3 | 65 | 3 | 3.25 | A = 33 B = 402 | 35.8 |
| 3.87 | 65 | 50.5[c] | 10.3 | 65 | 3 | 3.5 | A = 39 B = 480 | 35.4 |
| 4.53 | 110 | 50.5[c] | 10.3 | 65 | 3 | 2 | A = 35 B = 405 | 38 |

[a]80% of design capacity
[b]90% of design capacity
[c]70% of design capacity

Without the anode supports, the conversions were consistently low even at varying production levels (e.g., 80%, 90% and 70% of design capacity). The low conversion was believed to be due to differential pressure across the Nafion membrane which deflected the membrane toward the anode. The resulting channeled flow probably reduces the residence time, resulting in poor conversion.

EXAMPLE 2

Using the electrolytic generator of Example 1 with support ribbing for the cell's membrane, additional runs were carried out where the pH of the anolyte effluent varied. The results are shown in Table 3 below.

TABLE 3

| Power | | Anolyte | | Catholyte | | | Conversion | |
|---|---|---|---|---|---|---|---|---|
| | | Vacuum | | Pressure | | | $ClO_2$ | |
| Volts | Amps | gpd | (psig) | gpd | (psig) | pH | Titrations | (%) |
| 5.68 | 120 | 65[a] | 6.4 | 106 | 3 | 3 | A = 137 B = 930 | 69.1 |
| 5.5 | 97.5 | 65[a] | 6.4 | 106 | 3 | 3.75 | A = 52 B = 365 | 66.7 |
| 6.24 | 97.5 | 65[a] | 6.4 | 106 | 3 | 4.5 | A = 38 B = 333 | 51 |

[a]90% of design capacity

At the 90% of design capacity level the conversion decreased as the pH of the chlorine dioxide level increased.

EXAMPLE 3

Using the electrolytic generator of Example 1 with the supported ribbing for the cell's membrane, an additional run was carried out at 30% of design capacity. The results are shown in Table 4 below.

TABLE 4

| Power | | Anolyte | | Catholyte | | | Conversion | |
|---|---|---|---|---|---|---|---|---|
| | | Vacuum | | Pressure | | | $ClO_2$ | |
| Volts | Amps | gpd | (psig) | gpd | (psig) | pH | Titrations | (%) |
| 4.73 | 50 | 22[a] | 7.1 | 85 | 3 | 3 | A = 34 B = 272 | 57 |

[a]30% of design capacity

The results show that at pH 3 and 30% of design capacity the conversion was only 57%, whereas at pH 3 and 90% of design capacity the conversion was 69.1% (see Table 3).

EXAMPLE 4

Using the electrolytic generator of Example 3 with additional support ribbings for the cell's membrane (see FIG. 5), an additional run was carried out at 90% and 30% of design capacities. The results are shown in Table 5.

TABLE 5

| Power | | Anolyte | | Catholyte | | | Conversion | |
|---|---|---|---|---|---|---|---|---|
| | | Vacuum | | Pressure | | | $ClO_2$ | |
| Volts | Amps | gpd | (psig) | gpd | (psig) | pH | Titrations | (%) |
| 5.2 | 96.5 | 65[a] | 6.4 | 106 | 3 | 2.7 | A = 78 B = 520 | 71 |
| 5.2 | 96.5 | 65[a] | 6.4 | 106 | 3 | 2.8 | A = 112 B = 776 | 68 |
| 5.2 | 96.5 | 65[a] | 6.4 | 106 | 3 | 5.2 | A = 45 B = 334 | 63 |
| 5.2 | 96.5 | 22[b] | 6.4 | 106 | 3 | 2.4 | A = 185 B = 151 | 53 |

[a]90% of design capacity
[b]30% of design capacity

Similar to the previous example, at comparable pH values, operation at 90% of design capacity results in an improvement in yield over operation at the 30% of design capacity level. In either case, there was a notable improvement in yield with the use of the membrane support ribbing.

EXAMPLE 5

With the same electrolytic cell used in Example 4, the electrolytic generator was modified such that both the anolyte and catholyte feed were educted through the cell under vacuum. The results of this trial are outlined below in Table 6.

TABLE 6

| | 1 | 1 Duplication | 2 | 3 | 4 | 5 | 6 | 7 |
|---|---|---|---|---|---|---|---|---|
| Voltage | 6.3 | 6.3 | 6.7 | 6.64 | 6.85 | 4.66 | 5.28 | 5.56 |
| Amperes/#$ClO_2$ | 11 | 11 | 12.8 | 12.8 | 14 | 12 | 14 | 16 |
| pH of Anolyte | 7.44 | 7.44 | 6.9 | 6.75 | 3 | 7.6 | 6.7 | 1.9 |
| Free $ClO_2$ | 372 | 352 | 362 | 401 | 359 | 290 | 269 | 242 |
| % Conversion to Free $ClO_2$* | 62 | 63 | 67 | 73 | 75 | 68 | 75 | 77 |

*based on 100% of design capacity

Now that the preferred embodiments of the invention have been described in detail, various modifications and improvements thereon will become readily apparent to those skilled in the art. Accordingly, the spirit and scope of the present invention are to be limited only by the appended claims and not by the above specification

What is claimed is:

1. An electrolytic generator, operated under a vacuum, for producing a solution of chlorine dioxide in one pass by the electrolysis of an anolyte which is a buffered aqueous alkali metal chlorite solution, which comprises in combination:

a high surface area, porous anode with multiple electrode posts;

a corrosion-resistant, highly conductive cathode with multiple electrode posts;

a cation ion exchange membrane which separates the anode and the cathode and forms an anolyte compartment and a catholyte compartment;

an array of non-corrosive support ribbings for the cation exchange membrane;

a non-binding mesh spacer between the cation exchange membrane and the cathode;

catholyte and anolyte cell frames with inlet ports to the catholyte and anolyte compartments at the bottom of the cell frames, with outlet ports from the catholyte and anolyte compartments at the top of the cell frames, and with internal flow distribution headers enclosing the anolyte and catholyte compartments;

an anolyte infeed means for introducing the buffered aqueous alkali metal chlorite anolyte into the anolyte compartment, which infeed includes a line with a solenoid followed by a rotameter and a flow switch;

an inlet means for softened, deionized, or demineralized purge water which means includes a line with a solenoid followed by a rotameter and a flow switch, means is connected to the anolyte infeed line by a juncture and a line leading from the juncture to the anolyte inlet port;

a catholyte infeed means for introducing softened, deionized, or demineralized water to the catholyte port, which means includes a line with a solenoid followed by a rotameter and a flow switch;

an ascending anolyte outfeed means, connected to the cell frame at the top on the anolyte side, to remove the aqueous chlorine dioxide anolyte effluent from the anolyte outlet port;

an eductor connected to the anolyte outfeed means for creating a vacuum in the anolyte compartment by which the anolyte is drawn through the anolyte compartment;

a motive water infeed means for supplying water to the eductor;

a catholyte outfeed means, connected to the catholyte outlet port, to remove the alkaline hydroxide catholyte effluent containing entrained hydrogen, which means has a non-corrosive check calve before the eductor;

a sensor, connected to the anolyte outfeed means prior to the eductor, for monitoring the anolyte effluent;

a pressure switch on the motive water infeed means; and a DC power supply and an automatic current interrupter to prevent reverse current flow across the cell upon shutdown.

2. The generator of claim 1, further comprising a dilution water infeed means for introducing into the anolyte infeed line softened, deionized, or demineralized water and a juncture joining the dilution water infeed means and anolyte infeed means.

3. The generator of claim 2, further comprising an eductor connected to the catholyte outfeed line for creating a vacuum in the catholyte compartment; an eductor connected to the dilution water infeed means for creating a vacuum to draw the water into dilution water infeed means; and a sensor connected to the anolyte infeed means for monitoring the anolyte infeed.

4. The generator of claim 2, wherein the non-corrosive check valves are plastic check valves, and wherein the catholyte outfeed means is ascending.

5. The generator of claim 2, wherein the catholyte and anolyte infeed lines and the catholyte and anolyte outfeed lines are plastic tubings.

6. The generator of claim 5, wherein the plastic tubings are polypropylene tubings.

7. The generator of claim 2, wherein the anode is a fine fibrous conductive substrate.

8. The generator of claim 7, wherein the substrate is titanium, niobium, zirconium, tantalum, aluminum, tungsten, hafnium, mixtures thereof, or alloys thereof.

9. The generator of claim 8, wherein the substrate is coated with a electrocatalyst selected from precious metals, the oxides of platinum group metals, mixtures thereof, and alloys thereof.

10. The generator of claim 9, wherein the precious metal is platinum, silver, or gold and wherein the platinum group oxides are prepared from rutherium, rhodium, palladium, irridium, or osmium.

11. The generator of claim 2, wherein the anode is a segmented fibrous titanium coated with platinum and wherein the cathode is a perforated stainless steel plate.

12. The generator of claim 2, wherein the anode is an unsegmented fibrous titanium coated with platinum and wherein the cathode is a perforated stainless steel plate.

13. The generator of claim 1, further comprising an on/off valve for the motive water.

14. The generator of claim 1, further comprising an electrical panel containing a sensor, safety indicators, and operation controls.

15. The generator of claim 14, wherein the sensor is a pH meter.

16. The generator of claim 14 wherein the sensor is a conductivity probe.

17. The generator of claim 14 wherein the sensor is an oxidation-reduction potential probe.

18. The generator of claim 14, wherein the sensor is an amperometric detector.

19. The generator of claim 14, wherein the sensor is a colormetric absorption indicator.

* * * * *

UNITED STATES PATENT AND TRADEMARK OFFICE
CERTIFICATE OF CORRECTION

PATENT NO.    : 6,274,009 B1
DATED         : August 14, 2001
INVENTOR(S)   : Krafton et al.

It is certified that error appears in the above-identified patent and that said Letters Patent is hereby corrected as shown below:

Title page,
Item [73], Assignee, "International Dioxide Inc., North Kingston, RI (US)" should read -- International Dioxcide Inc., North Kingstown, RI (US) --.

Signed and Sealed this

Twenty-ninth Day of October, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO. : 6,274,009 B1  
DATED : August 14, 2001  
INVENTOR(S) : Brian D. Krafton et al.

It is certified that error appears in the above-identified patent and that said Letters Patent is hereby corrected as shown below:

Column 15,
Line 54, "calve" should read -- valve --.

Signed and Sealed this

Twenty-first Day of October, 2003

JAMES E. ROGAN
*Director of the United States Patent and Trademark Office*